United States Patent [19]

Chapman

[11] Patent Number: 4,843,169
[45] Date of Patent: Jun. 27, 1989

[54] METHOD OF PREPARING ALPHA-ARYLALKANOIC ESTERS

[75] Inventor: Robert C. Chapman, Manchester, Mo.

[73] Assignee: Mallinckrodt, Inc., St. Louis, Mo.

[21] Appl. No.: 888,539

[22] Filed: Jul. 21, 1986

[51] Int. Cl.$^4$ .............................................. C07C 69/76
[52] U.S. Cl. .................................... 560/105; 560/55; 560/66; 560/9
[58] Field of Search ............................ 560/105, 66, 9

[56] References Cited

U.S. PATENT DOCUMENTS 4,316,046  2/1982  Costa ................................... 560/105

FOREIGN PATENT DOCUMENTS 8021644  8/1983  Japan ................................... 560/105
59-163345  9/1984  Japan.

OTHER PUBLICATIONS

Tamura et al., *Synthesis*, pp. 231–232 (Mar. 1984).
A. Goosen and C. W. McCleland, *J. Chem. Soc., Chem. Commun.*, pp. 1311–1312 (1982).
Y. Hamada and T. Shioiri, *Tetrahedron Lett.*, 23(2), pp. 235–236 (1982).
S. D. Higgins and C. B. Thomas, *J. Chem. Soc., Perkin Trans. I*, pp. 235–242 (1982).
K. Fujii et al., *Synthesis*, pp. 456–457 (1982).
B. Myrboh et al., *Synthesis*, pp. 126–127 (1981).
G. Tsuchihashi et al., *Tetrahedron Lett.*, 22(43), pp. 4305–4308 (1981).
T. Shioiri and N. Kawai, *J. Org. Chem.*, 43(14), pp. 2936–2938 (1978).
A. McKillop et al., *J. Am. Chem. Soc.*, 95(10), pp. 3340–3343 (1973).

*Primary Examiner*—Paul J. Killos
*Attorney, Agent, or Firm*—Roy J. Klostermann; Lynden N. Goodwin

[57] ABSTRACT

Alpha-arylalkanoic esters are prepared by reacting a trivalent iodine compound of the formula

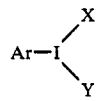

wherein Ar is an aromatic hydrogen and X and Y each represent a group which can be removed as an anion, with a carbonyl compound of the formula

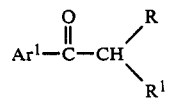

where $Ar^1$ is an aromatic hydrocarbon, R is a hydrogen atom or an alkyl group, and $R^1$ is a hydrogen atom or an alkyl group, in the presence of an orthocarboxylic ester having the general formula $ZC(OR^2)_3$, wherein $R^2$ is an alkyl group and Z is a hydrogen atom or an alkyl group; the reaction being carried out in the presence of sulfuric acid in an amount from about 0.2 to about 0.8 mole per mole of the carbonyl compound.

18 Claims, No Drawings

METHOD OF PREPARING ALPHA-ARYLALKANOIC ESTERS

TECHNICAL FIELD

The present invention relates to a method of preparing α-arylalkanoic esters.

BACKGROUND OF THE INVENTION

Alpha-arylalkanoic acids are widely used as active anti-inflammatory, analgesic, and anti-pyretic pharmaceutical products. Such acids include, for example, ibuprofen, 2-(4-isobutylphenyl)propionic acid and fenoprofen, 2-(3-phenoxyphenyl)propionic acid. Various methods are known in the art for making these acids and their corresponding esters. For example, α-arylalkanoic esters can be made from corresponding carbonyl compounds of the general formula:

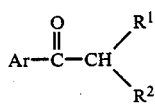

wherein at least one of the $R^1$ and $R^2$ groups is an alkyl group and the other is a hydrogen atom or an alkyl group or wherein $R^1$ is a bromine aton and $R^2$ is an alkyl group (*Journal Am. Chem. Soc.*, 95:3340 [1973]; *Synthesis*, p. 126, [1981]; *Synthesis*, p. 456, [1982]; *Parkin Transactions* (British Chem. Soc.), 1:235 [1982]; *Tetrahedron Letters*, 23:235 [1982], *Tetrahedron Letters* 22:4305 [1981]; *Journal Organic Chemistry*, 43:2936 [1978]; *Chemical Communications*, p. 1311, [1982].

Each of the aforementioned methods has at least one disadvantage, such as requiring the use of a poisonous thallium or lead salt or a precious, and expensive, silver salt, requiring a lengthy reaction time, and producing the desired product in low yields. Y. Tamura, Japanese Patent Publication No. Sho 59 [1984]-163,345, laid open Sept. 14, 1984, discloses a method of preparing α-arylalkanoic esters represented by the general formula

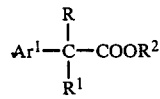

wherein $Ar^1$ is an aromatic hydrocarbon group, R and $R^1$ each represent a hydrogen atom or an alkyl group, and $R^2$ is an alkyl group, by reacting a compound of trivalent iodine having the general formula

wherein Ar is an aromatic hydrocarbon group and X and Y are each a group which can be eliminated as an anion, with a carbonyl compound having the general formula

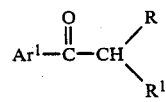

wherein $Ar^1$, R, and $R^1$ are as defined above. As disclosed therein, the reaction is effected in the presence of an orthocarboxylic ester having the general formula $ZC(OR^2)_3$, wherein $R^2$ is an alkyl group and Z is a hydrogen atom or an alkyl group. According to the Tamura disclosure, the reaction can be completed smoothly within a short period of time via heating in the presence of concentrated sulfuric acid. Example 1 thereof discloses heating and agitating 1 mmole of p-isobutylpropiophenone and 1 mmol of iodobenzene diacetate in 1.5 ml (13.7 mmol) o-formic acid methyl ester in the presence of 1 mmole concentrated sulfuric acid for 30 minutes to obtain ibupurophene [sic] methyl ester. Similarly, synthesis of methyl 2-arylpropanoates (such as the methyl ester of ibuprofen) from aryl ethyl ketones (such as p-isobutylphenyl ethyl ketone, i.e. p-isobutylpropiophenone) using diacetoxyphenyliodine (also known as iodobenzene diacetate) wherein the reaction is performed in trimethyl orthoformate in the presence of sulfuric acid (10 mmol per 5 mmol of ketone in typical procedure) is disclosed by Tamura et al., *Synthesis*, March 1984, 231–232. Although the method of Tamura (and co-workers) appears to eliminate one or more disadvantages of methods disclosed in the older art, it employs relatively large quantities of the orthocarboxylic ester, such as orthoformic methylester, a typically expensive reagent. Accordingly, there is a substantial need in the art for improvements in the above-described Tamura method, whereby the arylalkanoic ester compounds can be prepared using less orthoocarboxylic ester with resulting lower cost.

The present invention fulfills the above need by providing a low-cost improvement which reduces the amount of orthocarboxylic ester required in the Tamura method to prepare the arylalkanoic esters in good yield (e.g. at least 50% and often at least 70%). This beneficial result is surprisingly obtained by carrying out the reaction in the presence of a critical low amount of sulfuric acid.

DESCRIPTION OF THE INVENTION

In accordance with the present invention, α-arylalkanoic esters of the general formula

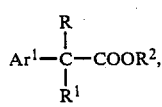

wherein $Ar^1$ is an aromatic hydrocarbon group, R and $R^1$ are each of a hydrogen atom or an alkyl group, and $R^2$ is an alkyl group, are prepared by reacting a compound of trivalent iodine having the general formula

wherein Ar is an aromatic hydrocarbon group and X and Y are each a group which can be eliminated as an anion, with a carbonyl compound having the general formula

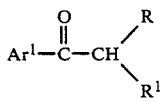

wherein Ar¹, R, and R² is an alkyl group and Z is a hydrogen atom or an alkyl group, and in the additional presence of sulfuric acid in a critically important amount from about 0.2 mole to about 0.8 mole per mole of the carbonyl compound of ketone. By conducting the reaction in such amount of sulfuric acid, a given yield of the arylalkanoic esters is obtainable with a lesser amount of orthocarboxylic ester than is required for such yield when the reaction is conducted in the presence of amounts of sulfuric acid outside such range, e.g. 1 or 2 moles per mole of ketone.

DETAILED DESCRIPTION OF THE INVENTION AND OF THE MANNER AND PROCESS OF MAKING AND USING IT

The present invention relates to a method of preparing a-arylalkanoic esters. In accordance with this method, the a-arylalkanoic esters are prepared by reacting a trivalent iodine compound with a carbonyl compound in the presence of an orthocarboxylic ester and a critical low amount of sulfuric acid, whereby the amount of orthocarboxylic ester required for the reaction is decreased, thus improving the economics of the reaction process.

By the method of this invention, a-arylalkanoic esters represented by the general formula

wherein Ar¹ is an aromatic hydrocarbon, R is a hydrogen atom or an alkyl group, R¹ is a hydrogen atom or an alkyl group, and R² is an alkyl group, are prepared by reacting a trivalent-iodine, compound represented by the general formula:

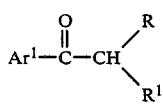

wherein Ar is an aromatic hydrocarbon group, and X and Y are each a group eliminated as an anion, with a carbonyl compound represented by the general formula:

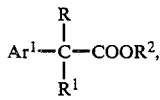

where Ar¹, R and R¹ are the same as defined above, in the presence of an orthocarboxylic ester represented by the general formula ZC(OR²)₃, wherein R² is an alkyl group and Z is a hydrogen atom or an alkyl group, and in the presence of sulfuric acid in an amount from about 0.2 mole to about 0.8 mole per mole of the carbonyl compound.

In this reaction process Ar represents an aromatic hydrocarbon group, which may have one or more substituents on the aromatic ring. The substituent may be a linear or branched alkyl group such as methyl, ethyl, nor iso-propyl, or n-, iso-, sec- or t-butyl group, an alkoxy group such as methoxy, ethoxy, n- or iso-propyloxy, or n-, iso-, sec- or t-butoxy group, an aryloxy group such as phenoxy, an acyloxy group such as acetoxy, n- or iso-propionyloxy, n-, iso-, sec- or t-butyloyloxy, or benzoyloxy group, or an electron attractive group such as a nitro, acetyl, propionyl, benzoyl, nitrile or sulfonyl-containing group.

Ar¹ also represents an aromatic hydrocarbon group which optionally may carry a substituent on the aromatic ring. The substituent may be a saturated hydrocarbon group such as an alkyl group having 1 to about 4 carbon atoms; an unsaturated aliphatic hydrocarbon group such as vinyl, ethynyl, or allyl group, an alkenyl or alkenyloxy group having such an unsaturated group; an alkoxy group such as methoxy, ethoxy, n- or iso-propyloxy, or n-, iso-, sec- or t-butoxy; an alkylthio group such as methylthio, ethylthio, n- or isopropylthio, or n-, iso-, sec- or t-butylthio; an arylthio group such as phenylthio; an aryl group, such as phenyl; a halogen atom or an amino group which is mono- or di-substituted by n- or iso-propyl, or n-, iso-, sec- or t-butyl group.

The groups R and R¹ may each independently represent an alkyl group, such as methyl, ethyl or propyl, or a hydrogen atom.

Preferably, the carbonyl compound is an acetophenone or propiophenone, the phenyl group of which optionally is substituted with an alkyl group, halogen or alkoxy group. The ratio of trivalent iodine compound to carbonyl compound desirably is at least 1:1. A preferred ratio is about 1:1.

In trivalent-iodine compounds

X and Y are groups which can be eliminated as an anion and including, for example, aliphatic and aromatic acyloxy groups such as acetoxy, trifluoroacetoxy, and benzoyloxy, and halogen atoms such as chloro and fluoro. X and Y may be the same group or different groups and may include a combination of an acyloxy group as X and a hydroxy group as Y.

The trivalent-iodine compounds can be produced in accordance with procedures well known in the art. For example, if X and Y are chlorine atoms,

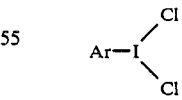

can be prepared by reacting an iodinated aromatic hydrocarbon, Ar-I, with chlorine. If the dichloro trivalent-iodine compound obtained is allowed to react with acetic acid, the chlorine can be replaced with an acetoxy group. In the same way other trivalent-iodine compounds having other electronegative groups also can be produced.

The reaction is carried out in the presence of an orthocarboxylic ester represented by the general formula CZ(OR²)₃. In this formula Z is a hydrogen atom or an alkyl group and $R^2$ is an alkyl group. Preferably, the compound is the methyl, ethyl or propyl ester of orthoformic acid. Ethyl orthoformate is especially preferred in comparison to other orthocarboxylic esters in that it is the most economical.

To obtain the desired a-arylalkanoic esters, the trivalent iodine compound and carbonyl compound are reacted together in the presence of the orthocarboxylic ester and sulfuric acid and in the presence or absence of an inert solvent. As used herein, "inert solvent" means a solvent which does not react with one or more of the trivalent iodine compound, the carbonyl compound and the orthocarboxylic ester or otherwise interfere with the reaction and in which each of the foregoing compounds is dispersible, with at least one of such compounds preferably being soluble in the solvent.

As a result of conducting the reaction in the presence of the above critical amount of sulfuric acid, the amount of orthocarboxylic acid needed is significantly decreased in comparison to the amount required when the reaction is conducted using sulfuric acid in higher and lower amounts. In Example 1 of Japanese Laid Open Patent Publication 163,345, wherein the molar ratio of sulfuric acid to the carbonyl compound is 1:1, the molar ration of orthocarboxylic ester to carbonyl compound is about 14:1. In accordance with the method of this invention, the molar ratio of orthocarboxylic ester to carbonyl compound can be as low as about 0.6:1. If desired, additional orthocarboxylic ester, sufficient to bring the amount to about three or more moles per mole of carbonyl compound, can be employed. Typically, no more than 6-8 moles of orthocarboxylic ester per mole of carbonyl compound are needed to obtain high yields of product.

The reaction is carried out in the additional presence of sulfuric acid in an amount from about 0.2 to about 0.8 mole per mole of the carbonyl compound or ketone. The amount of sulfuric acid is critical to obtain good yields of arylalkanoic esters at low molar ratios of orthocarboxylic ester to ketone. At given low molar ratios of orthocarboxylic esters to ketone (OCE:K), use of molar ratios of sulfuric acid to ketone above about 0.8:1 and below about 0.2:1 result in substantially lower yields of arylalkanoic esters than are obtainable at acid:ketone ratios from about 0.2:1 to about 0.8:1 for the same OCE:K molar ratio.

Where, as preferred, the reaction is carried out neat (i.e., in the absence of an inert solvent), the molar ratio of sulfuric acid to ketone is preferably from about 0.2:1 to about 0.5:1.

Where the reaction is conducted in the presence of an inert solvent (e.g. methylene chloride, toluene, and acetic acid), the molar ratio of sulfuric acid to ketone is preferably from about 0.2:1 to about 0.7:1, and more preferably is about 0.5:1.

The reaction is preferably carried out under substantially anhydrous conditions (e.g. not more than 0.5% by weight water in the reaction mixture based on the weight of carbonyl compound), thereby increasing the obtainable yield of the arylalkanoic ester.

The reaction may be carried out at any suitable temperature, including for example minus 5° C. or less to 80° C. or more. Preferably, the reaction is conducted at low temperature (e.g., from about minus 5° C. to about 30° C. and more preferably from 0° C. to about 20° C.). At low OCE:K molar ratios (e.g. 2.0:1 or less), low reaction temperature results in higher yield of the arylalkanoic ester than is obtainable at higher temperature (e.g. 5 to 10% higher yield). Advantageously, the reaction may be conducted with good results at room temperature (about 20°-25° C.).

Suitable solvents for use as the inert solvent optionally employed in carrying out the reaction include hydrocarbons halogenated hydrocarbons, lower aliphatic esters, lower aliphatic esters, lower aliphatic nitriles, lower aliphatic alcohols, lower aliphatic acids and nitroparaffin. "Lower" is defined herein to include compounds having about 5 or fewer carbon atoms.

Examples of the solvents include linear or cyclic hydrocarbons having about 5 to about 7 carbon atoms, such as n-hexane, cyclopentane, cyclohexane, benzene and toluene; linear or cyclic halogenated hydrocarbons having 1 to about 6 carbon atoms, such as chloroform, dichloromethane and chlorobenzene; lower alkylesters such as methyl, ethyl and propyl esters of a fatty acid having 1 to about 3 carbon atoms, such as formic acid, acetic acid and propionic acid; lower aliphatic ethers having about 2 to about 4 carbon atoms such as dimethyl ether, diethyl ether and methyl ethyl ether; lower aliphatic nitriles, such as acetonitrile and propionitrile; lower aliphatic alcohols having 1 to about 4 carbon atoms, including methanol, ethanol, n- or isopropanol, and t-butanol; lower fatty acids having 1 to about 3 carbon atoms, i.e., formic acid, acetic acid and propionic acid; and nitroparaffin having 1 to about 2 carbon atoms, such as nitromethane and nitroethane. Preferred solvents are toluene, acetic acid and dichloromethane (most preferred).

The solvents may be used singly or as a mixture of two or more. If solvent recovery is taken into consideration, use of a single solvent may be preferable for ease of recovery of the reaction product.

Illustrative of unsuitable solvents are lower aliphatic ketones such as acetone, amides of a lower fatty acid di-substituted with lower alkyl groups such as dimethyl formamide, and lower dialkyl sulfoxides such as dimethyl sulfoxide. Such solvents interfere with the reaction of the present invention which will not proceed substantially in their presence.

Reaction time is dependent upon the carbonyl compound chosen as a reactant. The completion of the reaction can be determined by thin layer chromatography (TLC) by measuring for the disappearance of carbonyl compound. The α-arylalkanoic ester produced by the reaction can be recovered from the reaction mixture in accordance with conventional methods.

In preferred embodiments, the reaction is carried out neat to prepare ibuprofen methyl ester using per mole of p-isobutylpropiophenone as the carbonyl compound, iodobenzene diacetate (1 mole) as the trivalent iodine compound, methyl orthoformate (0.9 mole or less) as the orthocarboxylic ester, about 0.2 to 0.5 mole of concentrated sulfuric acid, substantially anhydrous reaction conditions (i.e., not more than 0.5% water in the reaction mixture based on the weight of the diacetate), a reaction temperature from 0° C. to about 20° C. and a reaction time sufficient to obtain ibuprofen methyl ester in good yield (e.g. 70% or more).

The present invention is further illustrated by the following examples, which are provided for illustrative purposes only and are not to be construed as limiting. All parts, percents and other amounts throughout this disclosure are by weight unless otherwise indicated.

EXAMPLE 1

To a suspension of iodobenzene diacetate (322 grams(g), 1.0 mol) in a solution of p-isobutylpropiophenone (190 g, 1.0 mol) in trimethylorthoformate (109 ml, 1.0 mol) was added, dropwise, concentrated sulfuric acid (about 96% $H_2SO_4$, 10.7 ml, 0.2 mol) at 3° C. with stirring over 40 minutes. The resulting reaction mixture was stirred 6 hours at 0° C. to 15° C. The ensuing reaction was quenched by adding 200 ml deionized water. HPLC (high performance liquid chromatography) analysis of the resulting reaction product, comparing to an external standard, demonstrated 79% yield of ibuprofen methylester. The mixture obtained can be separated into an aqueous phase and an organic phase, followed by isolation of purified ibuprofen methyl ester from the organic phase by column chromatography or distillation. Alternatively, the crude ester can be hydrolyzed by treating with 50% aqueous sodium hydroxide, followed by extraction of the resulting aqueous phase with heptane. Acidification of the aqueous phase and recrystallization of the solid precipitate yields high-purity ibuprofen.

EXAMPLE 2

The procedure of Example 1 was followed with the exception that the amount of $H_2SO_4$ was 0.5 mol and the amount of trimethylorthoformate was 1.1 mol, resulting in 76% yield of ibuprofen methyl ester.

EXAMPLES 3-5

The procedure of Example 1 was followed with the exception that the amount of methyl orthoformate (MOF) was as shown in the table below and the mixture was stirred an additional 16 hours at 0° C. to 25° C. The resulting yield of ibuprofen methyl ester is also shown in the table.

| Ex. | MOF Amount | Yield |
|---|---|---|
| 3 | 0.9 mole | 72% |
| 4 | 0.7 mole | 59% |
| 5 | 0.6 mole | 51% |

EXAMPLE 6

The procedure of Example 2 was followed with the exception that the reaction mixture further included 600 ml of dichloromethane as solvent, and the reaction was run at room temperature (about 20°-25° C.). The yield of ibuprofen methyl ester was 76%.

EXAMPLES 7-9

The procedure of Example 6 was followed except that the amount of dichloromethane was one liter and the amount of sulfuric acid was as shown in the table below, wherein the resulting yield of ibuprofen methyl ester is also shown.

| Ex. | Amount of Sulfuric Acid | Yield |
|---|---|---|
| 7 | 0.2 mol | 65% |
| 8 | 0.7 mol | 69% |
| 9* | 1.0 mol | 42% |

*Comparative example (not of the invention)

Although the foregoing description has been given in terms of sulfuric acid, it is to be understood that good results may also be obtained with other acids such as aryl sulfonic acids (e.g., p-toluene sulfonic acid), alkyl sulfonic acids (e.g., methane sulfonic acid), perchloric acid and nitric acid (preferably of high concentration and, more preferably, fuming nitric acid). In general, all or part of the sulfuric acid in the above description may be replaced with one or more of the other acids, each at one gram-equivalent per one gram-equivalent of replaced sulfuric acid.

BEST MODE CONTEMPLATED

The best mode contemplated for carrying out this invention has been set forth in the above description, for example, by way of setting forth preferred materials and operating conditions, including but not limited to preferred ranges and values of amounts and other non-obvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. A method for preparing an α-arylalkanoic ester represented by the general formula

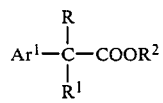

wherein $Ar^1$ is an aromatic hydrocarbon, R is an alkyl group or a hydrogen atom, $R^1$ is an alkyl group or a hydrogen atom, and $R^2$ is an alkyl group, which comprises reacting, under α-arylalkanoic ester-producing conditions, a trivalent iodine compound represented by the general formula

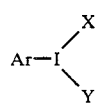

wherein Ar is an aromatic hydrocarbon and X and Y each represents a group which can be elimiated as an anion, with a carbonyl compound represented by the general formula

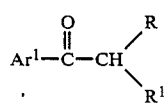

wherein $Ar^1$, R and $R^1$ are as defined above, in the presence of an orthocarboxylic ester represented by the general formula

wherein Z is an alkyl group or a hydrogen atom and $R^2$ is as defined above, and in the presence of sulfuric acid in an amount from about 0.2 mole to about 0.8 mole per mole of said carbonyl compound.

2. The method of claim 1 wherein the reaction is conducted in the absence of an inert solvent.

3. the method of claim 2 wherein the amount of sulfuric acid is from about 0.2 to about 0.5 mole per mole of said carbonyl compound.

4. The method of claim 1 wherein the reaction is conducted in the presence of an inert solvent.

5. The method of claim 4 wherein said solvent is selected from the group consisting of hydrocarbons, halogenated hydrocarbons, lower aliphatic esters, lower aliphatic ethers, lower aliphatic alcohols, lower aliphatic nitriles, lower aliphatic acids, nitroparaffin and compatible mixtures thereof.

6. The method of claim 5 wherein said solvent is selected from the group consisting of a linear or cyclic hydrocarbon comprising 5 to about 7 carbon atoms; a linear or cyclic halogenated hydrocarbon comprising 1 to about 6 carbon atoms; methyl, ethyl, n- or isopropyl ester of a fatty acid comprising 1 to about 3 carbon atoms; an aliphatic ether comprising about 2 to about 4 carbon atoms; an alkyl cyanide having 2 to about 3 carbon atoms; an aliphatic alcohol having 1 to about 4 carbon atoms; a fatty acid having 1 to about 3 carbon atoms and nitrated paraffin comprising 1 to about 2 carbon atoms.

7. The method of claim 6 wherein said solvent is selected from the group consisting of methylene chloride, toluene and acetic acid.

8. The method of claim 7 wherein said solvent is methylene chloride and the amount of sulfuric acid is from about 0.2 to about 0.7 mole per mole of said carbonyl compound.

9. The method of claim 8 wherein said amount is about 0.5 mole.

10. The method of claim 1 wherein Ar is a phenyl group which is optionally substituted by an alkyl, alkoxy, aryloxy, acyloxy or electron attractive group; X and Y are each a halogen atom or an aliphatic or aromatic acyloxy group; $Ar^1$ is a phenyl group which is optionally substituted by a saturated or unsaturated hydrocarbon, aryl, alkoxy, alkenyloxy, alkynyloxy, alkylthio, substituted amino group or a halogen atom; and R and $R^1$ are each a hydrogen atom or an alkyl group comprising one to three carbon atoms.

11. the method of claim 1 wherein Ar is a phenyl group which optionally is substituted by an alkyl group having 1 to about 4 carbon atoms, an alkoxy group having 1 to about 4 carbon atoms, a phenoxy group, an acyloxy group having 1 to about 4 carbon atoms, or an electron-attractive group selected from the group consisting of nitro, acetyl, propionyl, cyano, and sulfonyl-containing groups; X and Y each comprise a halogen atom or an aliphatic acyloxy group having about three or fewer carbon atoms; $Ar^1$ is a phenyl group which optionally is substituted by an alkyl group having 1 to about 4 carbon atoms, a phenyl group, an alkoxy group having 1 to 4 carbon atoms, a phenoxy group, an aliphatic acyloxy group, a benzoyloxy group, an alkylthio group having 1 to about 4 carbon atoms, or a mono- or di-substituted alkyl or phenyl amino group or a halogen atom; and R and $R^1$ each comprises a hydrogen atom or an alkyl group having 1 to 3 carbon atoms.

12. The method of claim 1 wherein said orthocarboxylic ester comprises methyl orthoformate, ethyl orthoformate, or propyl orthoformate.

13. The method of claim 1 wherein the molar ratio of said orthocarboxylic ester to said carbonyl compound is about 0.6:1 to about 8:1.

14. The method of claim 1 wherein the ratio of trivalent iodine compound to carbonyl compound is about 1:1 and the reaction is conducted at room temperature.

15. The method of claim 1 wherein the sulfuric acid is concentrated sulfuric acid.

16. The method of claim 1 wherein said carbonyl compound is p-isobutylpropiophenone, said iodobenzene compound is iodobenzene diacetate and said arylalkanoic ester is an ester of ibuprofen.

17. The method of claim 16 wherein said orthocarboxylic acid ester is methyl orthoformate and the ibuprofen ester is the methyl ester.

18. The method of claim 17 wherein said reaction is conducted under substantially anhydrous conditions in the absence of an inert solvent, the sulfuric acid is concentrated sulfuric acid and the amount of sulfuric acid is from about 0.2 to about 0.5 mole per mole of said carbonyl compound and the mole ratio of methyl orthoformate to said carbonyl compound is less than 1:1.

* * * * *

UNITED STATES PATENT AND TRADEMARK OFFICE
CERTIFICATE OF CORRECTION

PATENT NO. : 4,843,169

DATED : June 27, 1989

INVENTOR(S) : Robert C. Chapman

It is certified that error appears in the above-identified patent and that said Letters Patent is hereby corrected as shown below:

In the specification, Column 2, line 55, delete "of";

Column 3, line 7, after "R, and" insert --$R^1$ are as defined above, in the presence of an orthocarboxylic ester having the generic formula $ZC(OR^2)_3$, wherein--;

Column 4, line 3, delete "nor" and substitute --n- or--;

Column 4, line 44, delete "including" and substitute --include--.

In the claims, column 9, line 44, delete "comprising" and substitute --having--.

In the abstract, line 3, delete "hydrogen" and substitute --hydrocarbon--.

Signed and Sealed this

Twenty-first Day of August, 1990

Attest:

HARRY F. MANBECK, JR.

Attesting Officer

Commissioner of Patents and Trademarks